United States Patent [19]

Nakajima et al.

[11] 4,331,767
[45] May 25, 1982

[54] IMMOBILIZED ENZYME COLUMN

[75] Inventors: Takao Nakajima, Nara; Masafumi Terada, Higashiosaka; Tohru Mori, Ikeda, all of Japan

[73] Assignee: Fujisawa Pharmaceutical Co., Ltd., Osaka, Japan

[21] Appl. No.: 198,109

[22] PCT Filed: Sep. 4, 1979

[86] PCT No.: PCT/JP79/00234
§ 371 Date: Apr. 22, 1980
§ 102(e) Date: Apr. 22, 1980

[87] PCT Pub. No.: WO80/00574
PCT Pub. Date: Apr. 3, 1980

[30] Foreign Application Priority Data

Jun. 9, 1978 [JP] Japan ............................ 53/110102

[51] Int. Cl.³ .............................................. C12M 1/40
[52] U.S. Cl. ................................ 435/288; 422/82; 435/291
[58] Field of Search .................. 435/288, 287, 291; 422/82

[56] References Cited

U.S. PATENT DOCUMENTS

| 3,028,224 | 4/1962 | Ferrari, Jr. | 422/82 X |
| 3,047,367 | 7/1962 | Kessler | 422/82 X |
| 3,743,103 | 7/1973 | Isreeli et al. | 422/82 X |
| 3,811,841 | 5/1974 | Kassel | 422/82 |
| 3,826,615 | 7/1974 | Smythe et al. | 422/82 X |
| 4,188,466 | 2/1980 | Thinend et al. | 435/288 X |

FOREIGN PATENT DOCUMENTS

| 44-592 | 1/1969 | Japan . |
| 49-57893 | 6/1974 | Japan . |
| 52-43487 | 4/1977 | Japan . |
| 52-62088 | 5/1977 | Japan . |

Primary Examiner—Robert J. Warden
Attorney, Agent, or Firm—Oblon, Fisher, Spivak, McClelland & Maier

[57] ABSTRACT

An immobilized enzyme column useful for automatic chemical analyzers for analyzing substances contained in the blood serum, urine or the like with use of an enzyme for clinical tests includes at least one column main body (19, 34 or 44, 51 and 52). The column has a channel (31) extending from a sample inlet (24) to a sample outlet (27). An air bubble inlet (28) is disposed close to the sample outlet to communicate with the channel (31), and an air bubble outlet (25) is disposed close to the sample inlet to communicate with the channel. An immobilized enzyme accommodating portion (20 or 35) is provided in the channel between the bubble inlet (28) and the bubble outlet (25) and partitioned by a filter (29) at each end thereof.

12 Claims, 8 Drawing Figures

IMMOBILIZED ENZYME COLUMN

BACKGROUND OF THE INVENTION

1. Field of the Invention

This invention relates to an immobilized enzyme column useful for automatic chemical analyzers by which substances contained in the blood serum, urine or the like are analyzed in combination with an enzyme for clinical tests.

2. Description of the Prior Art

An immobilized enzyme column has a sample supply tube connected to its rear end and a sample discharge tube connected to its front end. Each of the tubes is divided, at a position close to the column, into two segments which are connected together by a three-way joint at two socket portions thereof. An air bubble removing tube is joined to the remaining one socket portion of the joint on the sample supply tube, and an air bubble supplying tube is joined to the remaining one socket portion of the joint on the sample discharge tube. Connected to a rear portion of the sample supply tube is an air supply tube for intermittently supplying air to divide a sample with air bubbles. When different samples are supplied to the column, a preceding sample will mingle with the following different sample, giving an inaccurate value on analysis. To avoid this, the sample is divided by air bubbles. In practice, however, it is difficult to interpose an air bubble accurately between the preceding sample and the following sample. Further if the sample passes through an immobilized enzyme with an air bubble incorporated in the sample, the bubble will diffuse through the sample, adversely affecting the analyzed value, so that there is the need to remove the bubble from the sample before the inlet to the portion of the column where the enzyme is accommodated and to supply an air bubble again to the sample after it has passed through the enzyme. Removal of the bubble nevertheless permits the preceding sample to mingle with the following sample and makes it meaningless to introduce the bubble into the sample. To eliminate such a problem, air is supplied to the same sample so that some dividing air bubbles will be present therein at specified spacing. While the immobilized enzyme accommodating portion in the column is spaced from the bubble removing tube and from the bubble supplying tube, the shorter the spacings, the better, because the longer the spacings, the longer will be the sections in which the preceding sample becomes mixed with the following one and the lesser will be the sample portion to be analyzed reliably. To compensate for this, there is the need to use an increased amount of sample which takes a longer period of time for analysis.

SUMMARY OF THE INVENTION

The immobilized enzyme columns according to this invention include at least one column main body, an air bubble inlet disposed close to a sample outlet to communicate with a channel extending from a sample inlet to the sample outlet, an air bubble outlet disposed close to the sample inlet to communicate with the channel, and an immobilized enzyme accommodating portion formed in the channel between the bubble inlet and the bubble outlet and partitioned by a filter at each end thereof. This arrangement minimizes the spacing between the immobilized enzyme accommodating portion in the column and an air bubble removing tube, and the spacing between the accommodating portion and an air bubble supplying tube, permitting analysis of a smaller quantity of sample with higher accuracy in a shorter period of time than heretofore possible.

The immobilized enzyme columns of this invention include one incorporating a plurality of column main bodies which are arranged side by side. The column main bodies adjacent to each other are formed on their opposed sides with open connecting portions which are connected together. This arrangement is convenient for using a plurality of kinds of enzymes at the same time without the necessity of interconnecting columns with a tube as heretofore done and further assures more accurate analysis than when enzymes are used in the form of a mixture. The arrangement is economical because when one of the enzymes has been inactivated earlier than the other, the column with the inactivated enzyme alone can be replaced.

DETAILED DESCRIPTION OF THE PREFERRED EMBODIMENT

This invention will be described below in greater detail with reference to the accompanying drawings.

Figure 1:
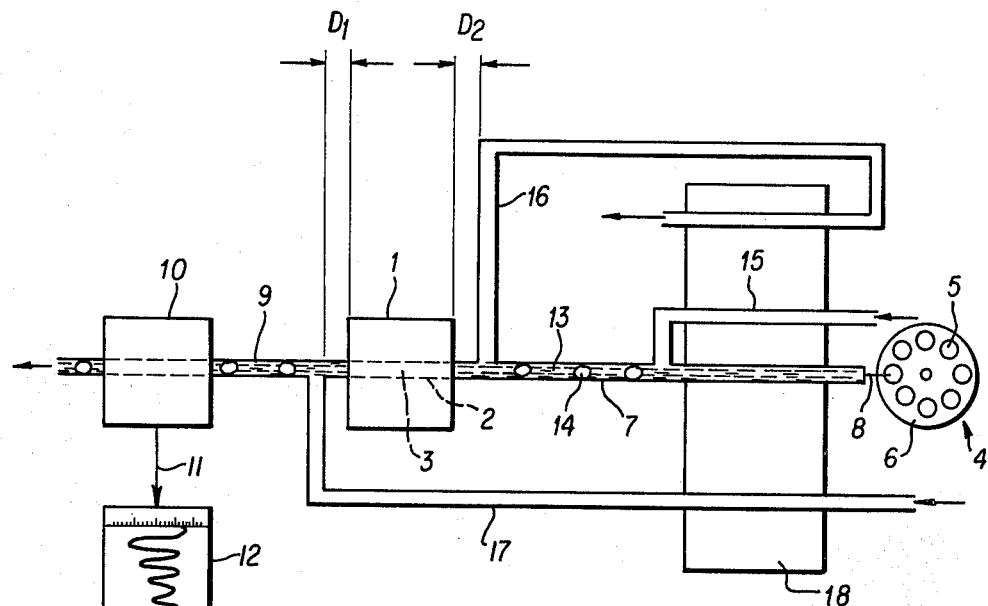
FIG. 1 is a diagram schematically showing an automatic chemical analyzer in its entirety.

FIG. 1 shows an automatic chemical analyzer in its entirety. An immobilized enzyme column 1 of the conventional type has an immobilized enzyme column accommodating portion 2 in the form of a horizontal channel extending through the center of the column. An enzyme 3 immobilized on a carrier, such as porous glass, is packed in the portion 2. A sampler 4 includes a circular table 6 intermittently rotatable and having a large number of sample cups 5 in its marginal portion. Connected to the rear end of the column 1 is the front end of a sample supply tube 7 having a rear end communicating with a sample cup 5 via a withdrawing member 8. Connected to the front end of the column 1 is the rear end of a sample discharge tube 9. A colorimeter 10 is provided between the front end outlet thereof and the rear end. The measurement obtained by the colorimeter 10 is sent as an electric signal 11 to a recorder 12. An air supply tube 15 for intermittently supplying air to divide a sample 13 with air bubbles 14 is connected to the supply tube 7 at a portion thereof close to its rear end. Each of the tubes 7, 9 is divided, at a position close to the column 1, into two segments which are connected together by a three-way joint at two socket portions thereof. An air bubble removing tube 16 is joined to the remaining one socket portion of the joint on the sample supply tube 7, and an air bubble supplying tube 17 is joined to the remaining one socket portion of the joint on the sample discharge tube 9. A metering pump 18 is associated with the tubes 7, 15, 16 and 17. The accommodating portion or horizontal channel 2 is spaced from the bubble removing tube 16 by a distance D1 and from the bubble supplying tube 17 by a distance D2.

Figure 2:
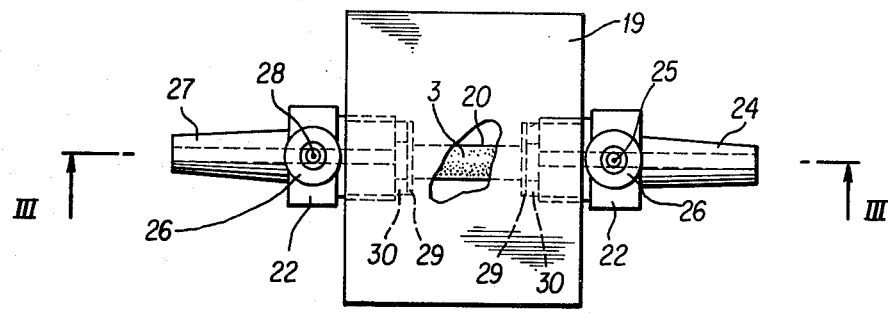
FIG. 2 is a plan view of an immobilized enzyme column of this invention comprising one column main body.
Figure 3:
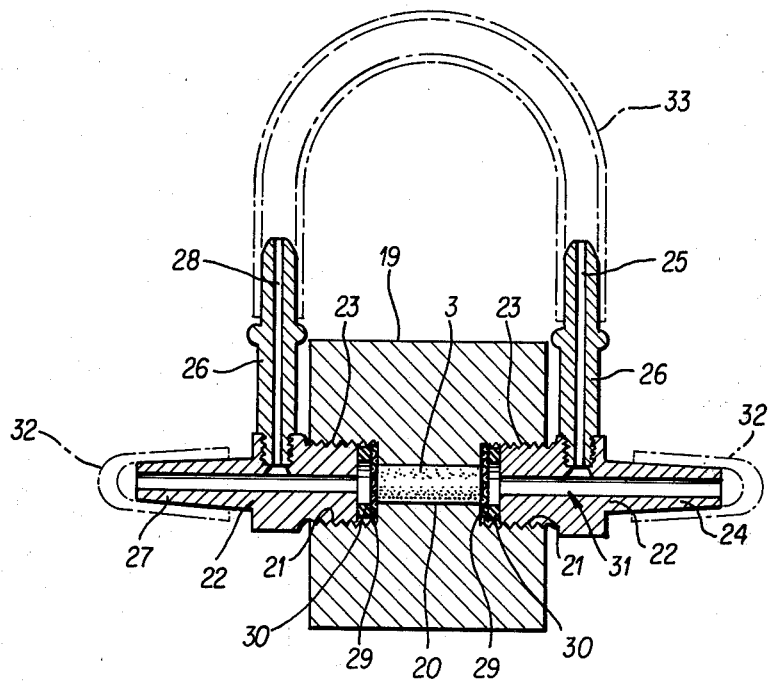
FIG. 3 is a view in section taken along the line III—III in FIG. 2.

FIGS. 2 and 3 show an immobilized enzyme column of this invention including one column main body. The main body 19 is rectangular parallelepipedal and is formed in its center with an immobilized enzyme accommodating portion 20 in the form of a horizontal hollow space. Formed in front and rear portions of the column main body 19 are internally threaded portions 21 communicating with the accommodating portion 20 and having a larger diameter than the portion 20. A tubular member 22 has at its base end an externally threaded portion 23 which is screwed into each of the internally threaded portions 21. The tubular member 22 on the rear side of the main body 19 has a forward end serving as a sample inlet 24. A nozzle 26 having an air bubble outlet 25 at its forward end is screwed into the same tubular member at a position close to the base end thereof. The tubular member 22 on the front side of the main body has a forward end serving as a sample outlet 27 and also has screwed in a portion thereof close to its base end a nozzle 26 having an air bubble inlet 28 at its forward end. Provided in the innermost part of each internally threaded portion 21 are a filter 29 and an annular packing 30 as arranged side by side. With the tubular members 22 screwed in the front and rear portions of the main body 19, the column has a channel 31 extending from the sample inlet 24 to the sample outlet 27. The accommodating portion 20 is formed in the channel 31, as partitioned by the filters 29 at its opposite ends. The portion 20 may have the immobilized enzyme 3 accommodated therein in advance, or may accommodate the enzyme 3 when the column is to be used. The column main body 19, tubular members 22 and nozzles 26 are all made of transparent rigid synthetic resin. For the identification of the enzyme in the column main body 19, the tubular members 22 and nozzles 26 are preferably colored in accordance with the kind of the enzyme. To prevent the activation of the enzyme 3 before the column is set on an analyzer, the sample inlet 24 and outlet 27 are each closed with a soft synthetic resin cap 32, and an inverted U-shaped bent tube 33 of soft synthetic resin is fitted at its ends to the bubble inlet 28 and outlet 25, as illustrated in broken lines in FIG. 3.

To incorporate the column of this invention into the analyzer, the caps 32 and tube 33 are removed, and the sample supply tube 7 is fitted to the sample inlet 24, the sample discharge tube 9 to the sample outlet 27, the air bubble supplying tube 17 to the bubble inlet 28, and the air bubble removing tube 16 to the bubble outlet 25.

Figure 8:
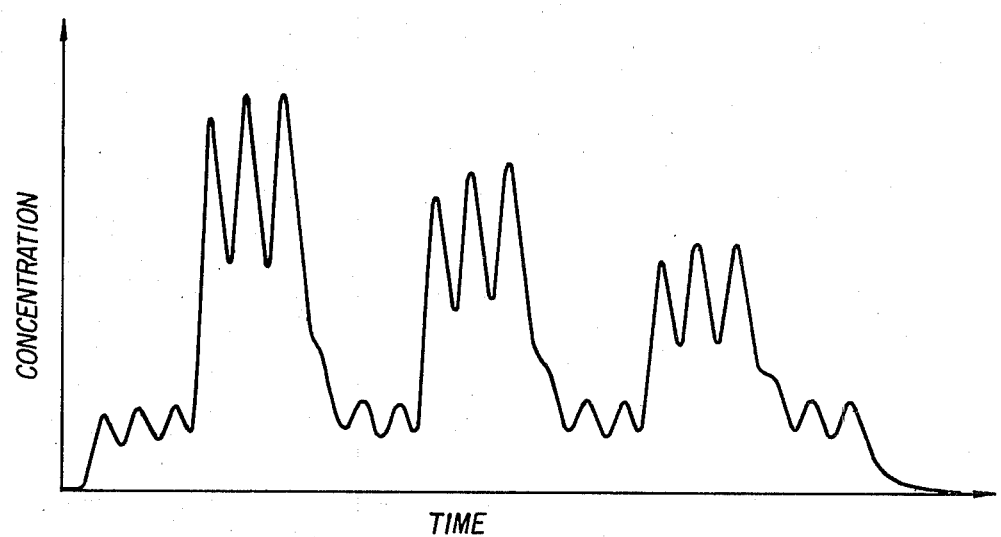
FIG. 8 is a graph showing the influence of a preceding sample on the following sample during analysis.

When different samples are supplied to the column, a preceding sample will affect the following sample. Aqueous solutions of glucose having varying concentrations are used as samples for the measurement of the concentrations, as shown in the table below. FIG. 8 shows the results, in which the concentration is plotted as ordinate vs. time as abscissa. The concentration curve shown is obtained by using a conventional immobilized enzyme column, alternately supplying a wash liquor (water) and then supplying the sample and also supplying three samples for each concentration. When samples of low concentration are followed by samples of high concentration, the first sample of high concentration is affected by the preceding sample of low concentration and exhibits a lower concentration than is specified. Conversely when samples of high concentration are followed by samples of low concentration, the first sample of low concentration is affected by the preceding sample of high concentration, exhibiting a higher concentration than is specified. After a sample of high concentration has been supplied, the wash liquor is of course fed to the column before a sample of low concentration is supplied, but the resulting wash liquor has a higher concentration than the sample of low concentration.

The following table shows the influence of preceding samples on the following samples as determined with use of the conventional immobilized enzyme column and the column of this invention for comparison. The sample supplied the third time, which has the specified concentration, is used as the standard to determine the influence of the preceding sample on the first sample, namely the degree of decrease or increase in the concentration. The immobilized enzyme accommodating portion is spaced from both the bubble removing tube and the bubble supplying tube by 10 cm in the case of the conventional column, and by 5 mm with the column of the invention shown in FIGS. 2 and 3.

| | Degree of influence (%) | |
| --- | --- | --- |
| Change of sample | Product of the invention | Conventional product |
| 100 mg/dl → 500 mg/dl | −0.8 | −5.1 |
| 500 mg/dl → 100 mg/dl | 17.4 | 55.0 |
| 100 mg/dl → 400 mg/dl | −2.7 | −8.4 |
| 400 mg/dl → 100 mg/dl | 16.5 | 44.0 |
| 100 mg/dl → 300 mg/dl | −4.6 | −5.9 |
| 300 mg/dl → 100 mg/dl | 7.1 | 26.5 |

The above table reveals that the degrees of influence of the preceding samples on the following samples are much smaller with the column of the invention than with the conventional column.

Figure 4:
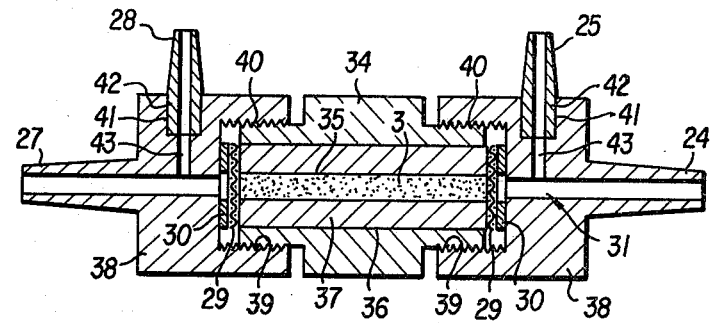
FIGS. 4 and 5 are sectional views corresponding to FIG. 3 and showing modified immobilized enzyme columns each comprising one column main body.
Figure 5:
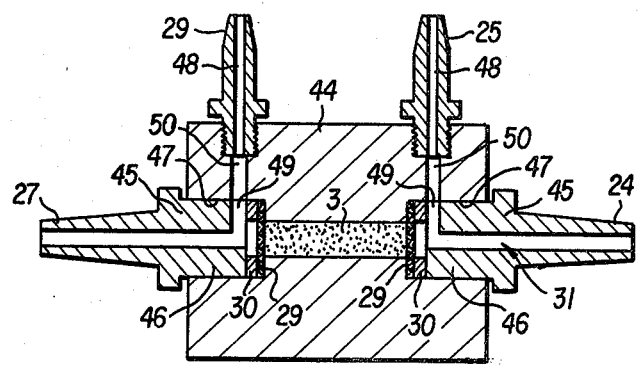

FIGS. 4 and 5 show modified immobilized enzyme columns of this invention each including one column main body. With the column shown in FIG. 4, a tube 37 is withdrawably inserted in a bore 36 extending through a column main body 34 to provide therein an immobilized enzyme accommodating portion 35. Two tubular members 38 have the same outside diameter as the column main body 34 except for a sample inlet 24 and a sample outlet 27 and each have an internally threaded portion 39. The internally threaded portions 39 are screwed on externally threaded portions 40 at the front and rear ends of the main body 34. A nozzle 42 has a base end intimately fitted in a cavity 41 formed in a top portion of each of the tubular members 38. Preferably the base end is bonded to the bottom of the cavity 41 with adhesive. The tubular members 38 are formed with passages 43 for causing an air bubble outlet 25 and an air bubble inlet 28 to communicate with a channel 31. If a filter 29 and a packing 30 are adhered to one end of the tube 37, it is convenient to place an immobilized enzyme 3 into the accommodating portion 35 of the tube 37 after withdrawing the tube 37 from the column main body 34. The main body 34 may be merely formed with a bore extending therethrough and serving as part of the channel 31 to thereby provide an accommodating portion for the immobilized enzyme.

The column shown in FIG. 5 has a column main body 44 which itself is similar in shape to the one shown in FIGS. 2 and 3. Each tubular member 45 has at its base end a straight tubular fitting portion 46 which is intimately fittable in a circular cavity 47 formed in the column main body 44. To place an immobilized enzyme 3 into an accommodating portion 20, the fitting portion 46 can be withdrawn from the cavity 47. Nozzles 48 having an air bubble outlet 25 and an air bubble inlet 28 are screwed in the top of the main body 44 to extend upward therefrom. Grooves 49 are formed in the base ends of the tubular members 45 to extend toward the nozzles 48. The main body 44 is formed with passages 50 for holding the grooves 49 in communication with the nozzles 48.

Figure 6:
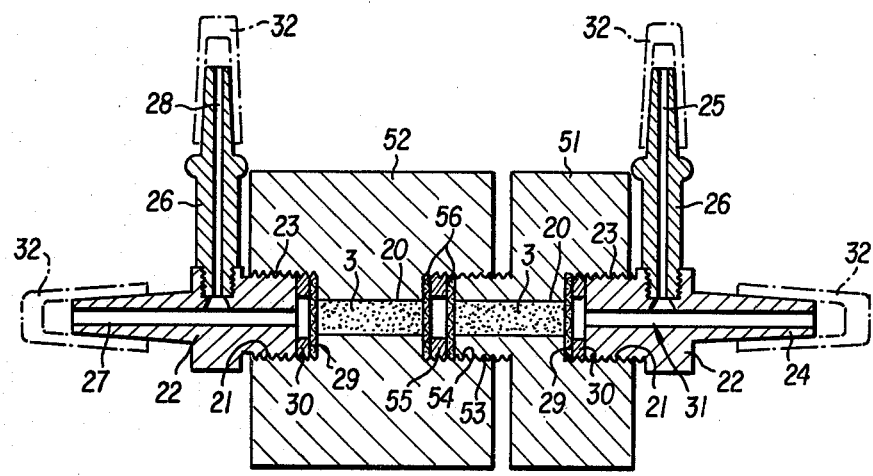
FIG. 6 is a sectional view corresponding to FIG. 3 and showing an immobilized enzyme column of this invention comprising two column main bodies.

FIG. 6 shows an immobilized enzyme column including two column main bodies according to this invention. The two main bodies 51, 52 of FIG. 6 themselves are similar in shape to the main body 19 shown in FIGS. 2 and 3 and are arranged with their channels in alignment. The main bodies 51, 52 adjacent to each other are formed on their opposed sides with open connecting portions 53, 54. The connecting portion 53 is provided with an externally threaded portion, while the other connecting portion has an internally threaded portion for the externally threaded portion to be screwed in. A packing 55 is sandwiched between filters 56, and the resulting assembly is interposed between these threaded portions screwed together, whereby the two column main bodies 51, 52 are joined together.

Figure 7:
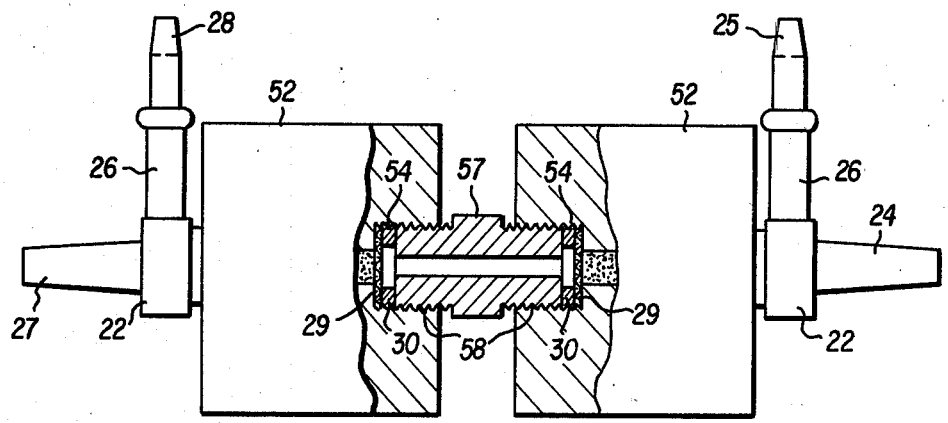
FIG. 7 is a side elevation partly broken away and showing a modification of the same column.

FIG. 7 shows a modification of the column of FIG. 6. Each of two column main bodies 52 has an internally threaded, open connecting portion 54. A tubular connecting member 57 has at its opposite ends externally threaded portions 58, which are screwed in the internally threaded portions, whereby the two column main bodies are connected together.

While FIGS. 6 and 7 each show two column main bodies which are connected together, at least three column main bodies can be connected together with use of an intermediate column main body having no tubular member.

What is claimed as new and desired to be secured by Letters Patent of the United States is:

1. An immobilized enzyme column apparatus having an immobilized enzyme for analyzing chemical samples in a chemical analyzer comprising:
   at least one column main body having a channel formed therethrough for accomodating said immobilized enzyme wherein said enzyme is disposed in said channel;
   sample inlet means having an inlet formed at an outer end portion thereof and having an inner end portion connected to said column main body;
   sample outlet means having an outlet formed at an outer end portion thereof and having an inner end portion connected to said column main body such that a flow path for said chemical samples is formed from said inlet means through said channel over said immobilized enzyme, and through said outlet means;
   an air bubble inlet nozzle operatively associated with and communicating with said outlet means and disposed proximate to said immobilized enzyme such that the distance between said inlet nozzle and said immobilized enzyme is minimized;
   an air bubble outlet nozzle operatively associated with and communicating with said inlet means and disposed proximate to said immobilized enzyme such that the distance between said inlet nozzle and said immobilized enzyme is minimized, and wherein said inlet nozzle, outlet nozzle and column main body are substantially integral and removable from said chemical analyzer as an integral unit; and
   a filter disposed at each end portion of said channel wherein each of said samples enters said sample inlet means, flows past said air bubble outlet nozzle into said column main body channel, past said air bubble inlet nozzle and exits through said outlet means.

2. The immobilized enzyme column of claim 1 further comprising a removable enzyme accommodating tube disposed within said channel.

3. The immobolized enzyme column of claim 1 further comprising means for mounting said inlet nozzle and said outlet nozzle on said column main body.

4. The immobilized enzyme column of claim 1 wherein said inlet means further comprises a first tubular member having means for detachably mounting said inlet means on said column main body and wherein said outlet means further comprises a second tubular member having means for detachably mounting said outlet means on said column main body.

5. The immobilized enzyme column of claim 4 wherein each of said first and second tubular members further comprises an externally threaded base portion and wherein said column main body further comprises internally threaded cavities formed therein for mating engagement with said first and second tubular members.

6. The immobilized enzyme column of claim 4 wherein each of said first and second tubular members further comprises an internally threaded base portion and wherein said column main body further comprises an externally threaded portion for mating engagement with said first and second tubular members.

7. The immobilized enzyme column of claim 4 wherein each of said first and second tubular members further comprises a base portion having a substantially smooth outer surface portion and wherein said column main body further comprises first and second cavities formed therein having substantially smooth walls for intimate engagement with said first and second tubular members, respectively.

8. The immobilized enzyme column of claim 4 wherein said first tubular member further comprises means for hermetically mating with said air bubble outlet and wherein said second tubular member further comprises means for hermetically mating with said air bubble inlet.

9. The immobilized enzyme column of claim 4 further comprising a packing member disposed between each said filter element and each of said first and second tubular members.

10. The immobilized enzyme column of claims 1, 4 or 9 wherein said at least one column main body further comprises first and second column main bodies and means for connecting said first and second column main bodies in seriatim.

11. The immobilized inzyme column of claims 10 wherein said connecting means further comprises an externally threaded outer surface portion on said first column main body and an internally threaded inner surface portion on said second column main body for engaging with said externally threaded outer surface portion on said first column main body.

12. The immobilized enzyme column of claim 10 wherein said connecting means further comprises a tubular connecting member having externally threaded outer surface portions provided on first and second end portions thereof, said first and second column main bodies further comprising first and second internally threaded inner surface portions for mating engagement with said first and second threaded end portions of said tubular connecting member, respectively, of said tubular member.

* * * * *

UNITED STATES PATENT AND TRADEMARK OFFICE
CERTIFICATE OF CORRECTION

PATENT NO. : 4,331,767
DATED : May 25, 1982
INVENTOR(S) : TAKAO NAKAJIMA ET AL.

It is certified that error appears in the above—identified patent and that said Letters Patent is hereby corrected as shown below:

Please correct as follows:

[30] --Foreign Application Priority Data

September 6, 1978 [JP] Japan.....53/110102 --

Signed and Sealed this

Third Day of August 1982

[SEAL]

Attest:

Attesting Officer

GERALD J. MOSSINGHOFF

Commissioner of Patents and Trademarks